United States Patent
Prisco et al.

(10) Patent No.: US 9,402,689 B2
(45) Date of Patent: *Aug. 2, 2016

(54) CONTROL SYSTEM FOR REDUCING INTERNALLY GENERATED FRICTIONAL AND INERTIAL RESISTANCE TO MANUAL POSITIONING OF A SURGICAL MANIPULATOR

(71) Applicant: Intuitive Surgical Operations, Inc., Sunnyvale, CA (US)

(72) Inventors: Giuseppe Maria Prisco, Calci (IT); David Q. Larkin, Menlo Park, CA (US); William C. Nowlin, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/932,117

(22) Filed: Nov. 4, 2015

(65) Prior Publication Data

US 2016/0051332 A1    Feb. 25, 2016

Related U.S. Application Data

(60) Continuation of application No. 14/490,090, filed on Sep. 18, 2014, now Pat. No. 9,198,730, which is a division of application No. 12/877,263, filed on Sep. 8, 2010, now Pat. No. 8,864,751, which is a continuation (Continued)

(51) Int. Cl.
*A61B 19/00* (2006.01)
*B25J 9/16* (2006.01)

(52) U.S. Cl.
CPC .............. *A61B 19/2203* (2013.01); *A61B 34/32* (2016.02); *A61B 34/75* (2016.02); *B25J 9/1638* (2013.01); *B25J 9/1641* (2013.01); *B25J 9/1689* (2013.01); *Y10S 901/02* (2013.01); *Y10S 901/15* (2013.01); *Y10S 901/28* (2013.01); *Y10S 901/30* (2013.01)

(58) Field of Classification Search
CPC ....................................................... A61B 19/22
USPC ....................................................... 606/1, 130
See application file for complete search history.

(56) References Cited

U.S. PATENT DOCUMENTS 6,574,355 B2    6/2003    Green
6,645,196 B1    11/2003   Nixon et al.

(Continued)

OTHER PUBLICATIONS

Bergamasco, Massimo et al., "An Arm Exoskeleton System for Teleoperation and Virtual Environments Applications," Proc. IEEE Int. Conf. on Robotics and Automation, 1994, pp. 1449-1454, vol. 2, IEEE.

(Continued)

*Primary Examiner* — William Thomson
*Assistant Examiner* — Jeffrey Lipitz

(57) ABSTRACT

A robotic control system is placed in clutch mode so that a slave manipulator holding a surgical instrument is temporarily disengaged from control by a master manipulator in order to allow manual positioning of the surgical instrument at a surgical site within a patient. Control systems implemented in a processor compensate for internally generated frictional and inertial resistance experienced during the positioning, thereby making movement more comfortable to the mover, and stabler from a control standpoint. Each control system drives a joint motor in the slave manipulator with a saturated torque command signal which has been generated to compensate for non-linear viscous forces, coulomb friction, cogging effects, and inertia forces subjected to the joint, using estimated joint angular velocities, accelerations and externally applied torques generated by an observer in the control system from sampled displacement measurements received from a sensor associated with the joint.

6 Claims, 7 Drawing Sheets

Related U.S. Application Data of application No. 11/479,144, filed on Jun. 30, 2006, now Pat. No. 7,819,859.

(60) Provisional application No. 60/751,916, filed on Dec. 20, 2005.

(56) References Cited

U.S. PATENT DOCUMENTS

| | | |
|---|---|---|
| 7,819,859 B2 | 10/2010 | Prisco et al. |
| 8,864,751 B2 | 10/2014 | Prisco et al. |
| 2002/0128552 A1 | 9/2002 | Nowlin et al. |
| 2003/0191454 A1 | 10/2003 | Niemeyer |
| 2004/0164960 A1 | 8/2004 | Jacobus et al. |
| 2005/0093821 A1 | 5/2005 | Massie et al. |
| 2007/0260356 A1 | 11/2007 | Kock et al. |
| 2015/0073435 A1 | 3/2015 | Prisco et al. |

OTHER PUBLICATIONS

Olsson, H. et al., "Friction Models and Friction Compensation," European Journal of Control, vol. 4, No. 3. Nov. 28, 1997, pp. 1-37.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

CONTROL SYSTEM FOR REDUCING INTERNALLY GENERATED FRICTIONAL AND INERTIAL RESISTANCE TO MANUAL POSITIONING OF A SURGICAL MANIPULATOR

CROSS REFERENCE TO RELATED APPLICATIONS

This application is a continuation of U.S. application Ser. No. 14/490,090(filed Sep. 18, 2014), now U.S. Pat. No. 9,198,730, which is a divisional of U.S. application Ser. No. 12/877,263 (filed Sep. 8, 2010), now U.S. Pat. No. 8,864,751, which is a continuation of U.S. application Ser. No. 11/479,144 (filed Jun. 30, 2006), now U.S. Pat. No. 7,819,859, which claims priority to U.S. provisional application Ser. No. 60/751,916 filed Dec. 20, 2005, each of which is incorporated herein by reference.

FIELD OF THE INVENTION

The present invention generally relates to robotic surgical systems and in particular, to a control system used in a robotic surgical system for reducing internally generated frictional and inertial resistance to manual positioning of a surgical manipulator.

BACKGROUND OF THE INVENTION

Robotic surgical systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using robotic surgical systems is strong and growing.

To perform a minimally invasive surgical procedure on a patient, one or more incisions are first made in the patient and cannulae inserted therein to gain access to a surgical site within the patient. Setup arms supporting the slave manipulators (or robotic arm assemblies) are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate master manipulators (or master input devices) which are coupled to the slave manipulators and their respective surgical instruments through one or more controllers to perform the surgical procedure.

The initial positioning and orientating of the surgical instrument at the surgical site is generally performed by an assistant, positioned next to the patient, manually moving a slave manipulator so as to move its surgical instrument into the proper position and orientation to and at the surgical site. Typically such positioning and orientating involves a two-step procedure in which, in a first part, the slave manipulator is attached to its assigned cannula and its surgical instrument engaged on it, and in a second part, the slave manipulator is manipulated so that its surgical instrument is properly positioned and oriented at the surgical site to perform its role in the minimally invasive surgical procedure. Although described as a two-part procedure, it is to be appreciated that the assistant may perform both parts concurrently or otherwise in an overlapping fashion, as well as sequentially so as to be performed one after the other.

To perform the first part of the initial positioning of a surgical instrument, the assistant depresses a first release button on a slave manipulator, which releases brakes holding setup joints of its corresponding setup arm in place so as to allow movement of the slave manipulator. The positioning of the slave manipulator is conventionally facilitated by the use of gravity-balanced or non-gravity loaded setup joints. After the slave manipulator is positioned so that it can be attached to its assigned cannula and is attached to it, the assistant may then stop depressing the first release button, which causes the brakes to hold their corresponding setup joints in place, thus locking the translational position of the cannula attached to the slave manipulator at this point. Additional details in performing this part of the procedure and the general construction of slave manipulators and their setup arms as pertaining to such procedure are provided in commonly owned U.S. Pat. No. 6,246,200 entitled "Manipulator Positioning Linkage for Robotic Surgery," which is incorporated herein by this reference.

To perform the second part of the initial positioning of the surgical instrument, the assistant engages the surgical instrument onto the slave manipulator so that it is capable of inserting it into the cannula, pivoting the instrument around a pivot point located at the surgical port of the cannula, and driving an end effector at the distal end of the surgical instrument with degrees of freedom resembling wrist motion. It may be noted at this point that the surgical instrument tip is inside the cannula and thus, is no longer visible to the assistant since it is now shielded by the anatomy.

To proceed, the assistant depresses a second button on or proximate to its slave manipulator, which disengages active joints of the slave manipulator from being controlled by their associated master manipulator. This allows the assistant to freely move the slave manipulator to insert the surgical instrument into its cannula and pivot about it about the incision so as to point in the proper direction and at the proper distance into the incision. If an endoscope has been previously positioned in the patient to view the surgical site, typically this step is performed while the assistant views the image of the surgical site provided by the endoscope. After the surgical instrument is thus positioned at the surgical site, the assistant may then stop depressing the second button, which allows the surgeon to re-engage control of the active joints of the slave manipulator through the master manipulator so that the surgeon may perform the surgical procedure by manipulating the master manipulator. To facilitate the positioning tasks described above, the first and second buttons may be effective only while they are depressed (and thus work as momentary buttons) or they can remain effective after they are released until they are depressed again (and thus work as toggle buttons).

Since the first part of the positioning procedure is performed by moving the gravity-balanced setup joints or non-gravity loaded setup joints outside of the patient's body, internally generated frictional and inertial resistance against manual movement of the slave manipulator is not generally objectionable to the assistant. In the second part of the positioning procedure, however, internally generated frictional and inertial resistance against manual movement of the slave manipulator may be objectionable to the assistant, because a finer control of the instrument tip is required while it is moved inside the surgical cavity. To facilitate easy movement of the slave manipulator during the second part of the positioning procedure, the arm may be mechanically gravity balanced using, for example, counter balance weights, so as to significantly reduce gravity effects and consequently, the force necessary for a person to physically move the slave manipulator. Additionally, the slave manipulator may be designed so as to have very high mechanical efficiency so that the friction does not change much with the force applied to the manipulator, have low friction forces or torque to overcome when moving the manipulator, and have low mass or inertia so that the manipulator may be accelerated with low force or torque.

Although a slave manipulator that does not have all of these mechanical characteristics may not be easy to manually position quickly and accurately, it may be advantageous to give away some of these mechanical characteristics in exchange for other benefits such as larger workspace, smaller footprint, or lighter slave manipulator. In such a design, a control system that is capable of recovering the lighter feeling of the mechanically gravity balanced design is desirable.

OBJECTS AND SUMMARY OF THE INVENTION

Accordingly, an object of aspects of the present invention is a control system for reducing internally generated frictional and inertial resistance to manual positioning of the slave manipulator.

This and additional objects are accomplished by the various aspects of the present invention, wherein briefly stated, one aspect is a robotic surgical system comprising a slave manipulator and a controller. The slave manipulator has jointed structures for providing multiple degrees of freedom movement to a surgical instrument when the instrument is coupled to the slave manipulator, joints corresponding to the jointed structures, motors to drive movement of the joints, and sensors to measure movement of the joints. The controller is configured with at least one control system generating a signal by processing measurements received from a corresponding one of the sensors to drive a corresponding one of the motors so as to reduce internally generated frictional and inertial resistance when manually moving at least a portion of the slave manipulator in order to position and/or orientate the surgical instrument at a surgical site within a patient.

Another aspect is a method for reducing internally generated frictional and inertial resistance when manually moving a slave manipulator, comprising: receiving sampled displacement measurements corresponding to movement of a joint in the slave manipulator; generating a first signal to compensate for internally generated non-linear viscous friction when manually moving the slave manipulator; generating a second signal to compensate for internally generated Coulomb friction when manually moving the slave manipulator; generating a third signal to compensate for internally generated inertial resistance when manually moving the slave manipulator; generating a fourth signal by adding or combining at least the first, second, and third signals; and driving a motor corresponding to the joint using the fourth signal.

In still another aspect, a robotic surgical system includes a slave manipulator which is coupled to a surgical instrument. The slave manipulator is configured so as to have a plurality of joints, a plurality of motors driving the joints, and a plurality of sensors for detecting motion of the joints. Also in the robotic surgical system is a control system comprising: an observer coupled to one of the sensors and configured to estimate at least an angular or linear velocity and acceleration of the joint corresponding to the sensor; and a signal generator configured to generate a signal to drive the motor corresponding to the joint so as to reduce internally generated frictional and/or inertial resistance when manually moving at least a portion of the slave manipulator in order to position or orientate the surgical instrument.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
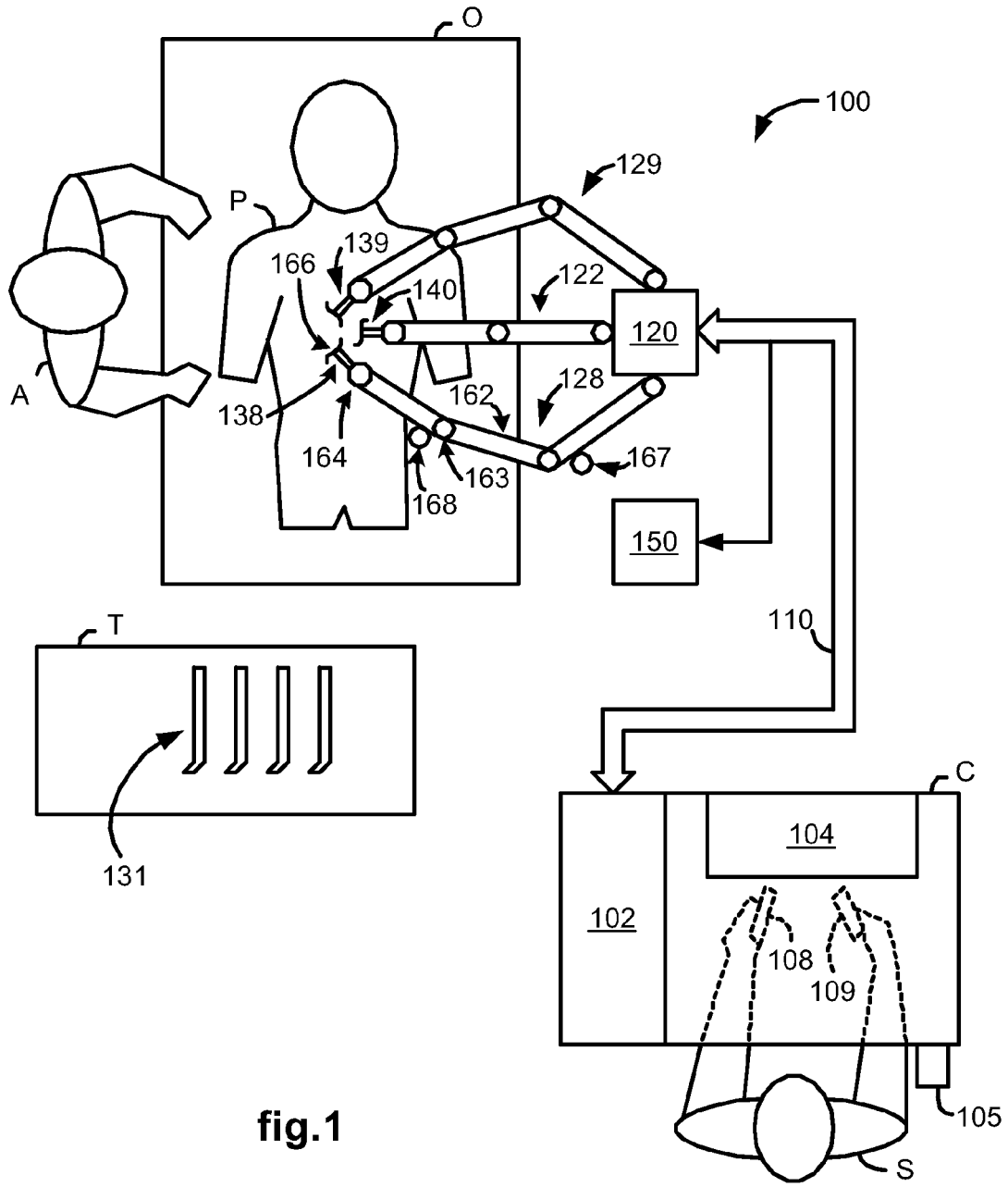
FIG. 1 illustrates a top view of an operating room employing a robotic surgical system utilizing aspects of the present invention.

FIG. 1 illustrates, as an example, a top view of an operating room employing a robotic surgical system. The robotic surgical system in this case is a Minimally Invasive Robotic Surgical (MIRS) system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 104 for displaying an image of a surgical site to the Surgeon, one or more manipulatable master manipulators 108 and 109 (also referred to herein as "control devices" and "input devices"), and a controller 102. The control devices 108 and 109 may include any one or more of a variety of input devices such as joysticks, gloves, trigger-guns, hand-operated controllers, or the like. The controller 102 is a personal computer that may be integrated into the Console or positioned next to it.

The Surgeon performs a minimally invasive surgical procedure by manipulating the control devices 108 and 109 so that the controller 102 causes their respectively associated slave manipulators 128 and 129 (also referred to herein as "robotic arms" and "robotic arm assemblies") to manipulate their respective removably coupled surgical instruments 138 and 139 (also referred to herein as "tools") accordingly, while the Surgeon views the surgical site in 3-D as it is captured by a stereoscopic endoscope 140 on the Console monitor 104.

Each of the tools 138 and 139, as well as the endoscope 140, is preferably inserted through a cannula or other tool guide (not shown) into the Patient so as to extend down to the surgical site through a corresponding minimally invasive incision such as incision 166. Each of the robotic arms is conventionally formed of linkages, such as linkage 162, which are coupled together and manipulated through motor controlled joints, such as joint 163.

The number of surgical tools used at one time and consequently, the number of robotic arms being used in the system 100 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 131 from a Tray ("T") in the operating room.

Preferably, the monitor 104 is positioned near the Surgeon's hands so that it will display a projected image that is oriented so that the Surgeon feels that he or she is actually looking directly down onto the operating site. To that end, an image of the tools 138 and 139 preferably appear to be located substantially where the Surgeon's hands are located even though the observation points (i.e., the endoscope or viewing camera) may not be from the point of view of the image.

In addition, the real-time image is preferably projected into a perspective image such that the operator can manipulate the end effector of a tool through its corresponding control device as if viewing the workspace in substantially true presence. By true presence, it is meant that the presentation of an image is a true perspective image simulating the viewpoint of an operator that is physically manipulating the tools. Thus, the processor 102 transforms the coordinates of the tools to a perceived position so that the perspective image is the image that one would see if the endoscope 140 was located directly behind the tools.

The processor 102 performs various functions in the system 100. One important function that it performs is to translate and transfer the mechanical motion of control devices 108 and 109 to their respective robotic arms 128 and 129 through control signals over bus 110 so that the Surgeon can effectively manipulate their respective tools 138 and 139. Another important function is to implement various control system processes.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

When it is desired to position and orientate a surgical instrument at the surgical site before starting a minimally invasive surgical procedure, the Assistant may depress a first Release Button 167 in order to move the setup arm of the slave manipulator 128 so that he or she may position the manipulator 128 so as to be attachable to a cannula extending into the incision 166. At the same time or afterwards, the Assistant may also engage the surgical instrument 138 onto the manipulator 128 and depress a second Button 168 in order to move the slave manipulator 128 so that he or she may insert the instrument 138 through the cannula to the surgical site and pivot the surgical instrument 138 into the proper position and orientation at the surgical site.

The first Release Button 167 releases brakes that hold or lock setup joints (which are generally passive joints) of the setup arms in place. There is no need to disengage control of the corresponding master manipulator at this time, if the master manipulator does not directly control the set-up joints. In such case, they are only intended to be moved manually when their breaks are released. After the surgical instrument is properly engaged on the manipulator 128 and is ready to be inserted into its assigned cannula, the setup joints and consequently, the setup arm of the slave manipulator 128, are then locked in place by the Assistant releasing the first Release Button 167. To facilitate its movement by the Assistant, a handle may be placed on the setup arm and the first Release Button 167 placed on the handle so as to be depressed by a thumb of the Assistant when gripping the handle.

The second Button 168 places the slave manipulator 128 and its associated master manipulator in a "Clutch Mode" by disengaging control of the slave manipulator 128 by the master manipulator, so that after the instrument 138 is engaged on the slave manipulator 128, the insertion axis is freed together with the Outer Yaw and Outer Pitch joints, and is under the control of the Assistant.

If an endoscope 140 has already been properly inserted into the Patient in order to generate images of the surgical site, the Assistant may perform this step by viewing the surgical site through a monitor 150 which is being fed images of the surgical site by the endoscope 140. On the other hand, if it is the endoscope 140 that is being inserted in this step, images generated by the endoscope 140 as it is being inserted, may be viewed on the monitor 150 by the Assistant.

Once inserted to the proper depth, the Assistant may then position the instrument 138 by moving the slave manipulator 128 so as to pivot the instrument 128 about a pivot point defined at the incision 166 or to insert it further along the cannula direction. After properly positioning and orientating the surgical instrument 138 at the surgical site, the Assistant may then release the second Button 168 to re-engage computer control of the slave manipulator 128 and in particular, its active joints, after the processor 102 has associated the current position of the surgical instrument 138 and its slave manipulator 128 with the locked position of its associated master manipulator. At this point, the slave manipulator will stay locked in place until the Surgeon acts to regain tele-control of it.

During manual positioning of the slave manipulator 128 by the Assistant, internally generated (i.e., within the slave manipulator 128) frictional and inertial resistance to such movement may become objectionable so as to make it difficult for the Assistant to manually position the surgical instrument 138 at the surgical site. To reduce such internally generated frictional and inertial resistance, a control system 200 is switched in to be operative during Clutch Mode.

Figure 2:
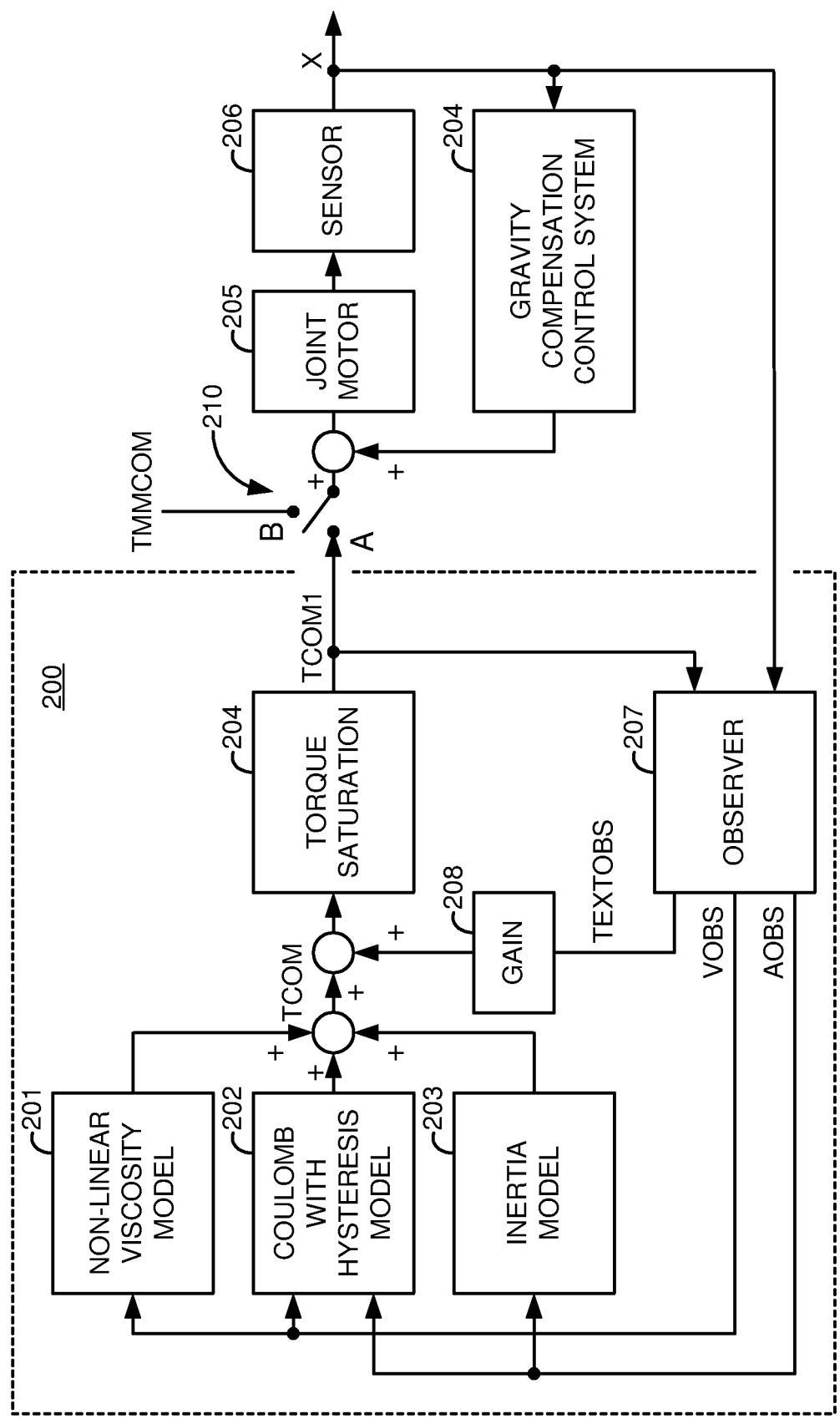
FIG. 2 illustrates a block diagram of a control system for reducing internally generated frictional and inertial resistance to manual positioning of a slave manipulator, utilizing aspects of the present invention.

FIG. 2 illustrates, as an example, a block diagram of a control system 200 for reducing internally generated frictional and inertial resistance to manual positioning of the slave manipulator 128. One or more of such control systems 200 (each providing frictional and inertial resistance countering torque commands to a corresponding joint motor) are preferably activated during Clutch Mode to assist the Assistant in positioning and/or orienting the surgical instrument 138 at the surgical site while the Assistant is viewing 2-D images generated from a right or left camera of the stereoscopic endoscope 140 in the monitor 150.

In the present example, one or more of such control system 200 is implemented in the processor 102 for the slave manipulator 128. The number of control system 200 included or otherwise activated for the slave manipulator 128 during Clutch Mode depends upon the number of active joints of the slave manipulator 128 which could materially benefit from such control system 200 in assisting the Assistant to reduce one or more sources of frictional and/or inertial resistance when manually moving the slave manipulator 128. The joint motor 205 and sensor 206, on the other hand, are included in the slave manipulator 128 to respectively drive and measure displacement of their corresponding active joint in the slave manipulator 128.

In its basic operation, when an Assistant manually moves the slave manipulator 128, the movement causes certain of its active joints to be rotated depending upon the directional and angular movement of the slave manipulator 128. Both gravitational, as well as internally generated frictional and inertial resistance to manual movement of the slave manipulator 128, may disturb the Assistant in this case. The control system 200 is designed to counteract undesired frictional and inertial forces.

In case the slave manipulator has a gravity imbalance, a separate Gravity Compensation control system 204 including a Gravity Model of the slave manipulator 128 may be used to counteract such gravity imbalance, and its torque commands added to those generated by the control systems 200 for appropriate active joint motors.

A Gravity Model based on a rigid body model for the links of a serial manipulator is a well known model in robotics. The gravity torque on the ith joint of the manipulator $grav\_i$ is computed as a function of the n×1 vector of current joint positions pos according to the formula:

$$grav\_i(pos) = \text{Sum (for } j \text{ from } I \text{ to } n)$$
$$(mass\_j * g \cdot Jac\_col\_j)$$

where $mass\_j$ is the mass of the jth link of the manipulator, g is the 3×1 vector of gravity acceleration, "·" indicates a vector scalar product, "*" indicates multiplication by scalar, and $Jac\_col\_j$ is given by the following expressions:

$$Jac\_col\_j = z\_j$$

for linear or prismatic joints, and $$Jac\_col\_j = z\_j \char`^ (P\_cog\_i - P\_j)$$

for revolute joints, where ^ indicates the vector cross product, $P\_cog\_i$ is the 3×1 vector representing the position of the center of mass of the ith link and $P\_j$ is the 3×1 vector representing a point on the axis of motion of the jth joint, and $z\_j$ represents the axis of the jth joint and more specifically, the unitary vector oriented for a prismatic or linear joint as the direction of linear motion of the joint and for a rotary joint as the axis of rotation of the joint.

A switch 210 is placed in the "A" position by the processor 102 during Clutch Mode (i.e., when the second Button 168 is depressed) in order to connect the control system 200 to its active joint motor 205. In Normal Mode (i.e., when the second Button 168 is not depressed), the switch 210 is placed in the "B" position so that a motor command signal TMMCOM from a master/slave control system (not shown) is provided to the active joint motor 205. The master/slave control system provides operative control of the slave manipulator 128 by its associated master manipulator during normal operation of the Robotic Surgical System 100. Additional details on such a master/slave control system are provided in commonly owned U.S. Pat. No. 6,424,885 entitled "Camera Referenced Control in a Minimally Invasive Surgical Apparatus," which is incorporated herein by this reference. Note that unlike the control system 200, the Gravity Compensation control system 204 is always connected to the active joint motor 205, in both Clutch and Normal Modes.

The internally generated frictional and inertial resistance to be overcome when manually moving the slave manipulator 128 may derive at least in part from viscosity of fluid material (such as grease) disposed on moving parts of the slave manipulator 128, Coulomb friction generated by the interaction of moving parts of the slave manipulator 128, cyclical cogging effects, and inertia of the moving parts of the slave manipulator 128. Thus, a properly scaled, compensating torque command signal is generated and provided to appropriate active joint motors by control systems 200 to assist the Assistant when manually moving the slave manipulator 128.

For each active joint being controlled by a control system 200 in the slave manipulator 128, an observer 207 corresponding to that active joint receives sampled displacement measurements "X" for the joint from its displacement sensor 206 and the joint motor torque command TCOM1 of the control system 200, and generates estimates for the angular velocity "VOBS", angular acceleration "AOBS", and external torque bias TEXTOBS.

A non-linear viscosity model 201 generates a first signal using the estimated velocity "VOBS", a Coulomb with hysteresis and cogging compensation model 202 generates a second signal using the sampled displacement measurements "X" for the joint along with the estimated velocity "YOBS" and acceleration "AOBS", and an inertia model 203 generates a third signal using the estimated joint acceleration "AOBS" and optionally, also using the position, estimated velocity and estimated acceleration of other active joints of the slave manipulator 128. The first, second and third signals are then combined or added together to generate a first torque command signal "TCOM". The external torque bias "TEXTOBS" is then scaled by a gain 208 that controls the amount of servo assist provided and is tuned experimentally to provide the desired lightness of feel to the operator moving the manipulator without inducing a feeling of activeness i.e. the feeling that the manipulator tends to move away on its own once its motion is manually initiated. The result is added to the first torque command signal "TCOM", and the sum passed through a torque saturation unit 204 (e.g., a limiter) to generate a second torque command TCOM1. The second torque command TCOM1 is then added, during Clutch Mode, to a gravity compensating torque command generated by the Gravity Compensation control system 204, and provided to the joint motor 205 as part of a drive signal.

The observer 207 used in the control system 200 is an estimator of the current state of a dynamic system that is chosen to model the dynamic behavior of interest of the active joint being controlled. The model used in this case is referred to a "Dynamic Joint Model".

A first Dynamic Joint Model that proves itself useful for the estimation of the joint velocity, joint acceleration and the external torque applied to the joint is a third order dynamic system representing a rigid mass or inertia feeling a viscous drag force linearly proportional to its velocity and an externally applied constant bias torque (External Torque). Choosing as system states the joint position, the joint velocity and the External Torque, and as system input the torque applied by the motor to the joint (Motor Torque), the first Dynamic Joint Model can be described in state space:

$$dx(t)/dt = Ax(t) + Bu(t)$$

$$y(t) = Cx(t)$$

wherein the input u is a scalar representing the Motor torque; the output y is a 3×1 column vector with first element being the joint position, second element being the joint velocity and third element being the External Torque; the state x is a 3×1 column vector with first element being the joint position, second element being the joint velocity and third element being the External Torque; A is a 3×3 matrix (state matrix) given by:

$A = [[0\ 1\ 0][0\ -b/m\ 1/b][0\ 0\ 0]]$, where m is the total joint mass or inertia, and b is the total coefficient of linear viscous friction of the joint; B is a 3×1 column vector given by:

$B = [0\ 1/m\ 0]$;

and C is a 3×3 identity matrix:

$C = [1\ 0\ 0;\ 0\ 1\ 0;\ 0\ 0\ 1]$.

The transfer function G(s) between the joint position and the joint motor torque can be expressed using the Dynamic Joint Model presented above as:

$G(s) = 1/(m*s+b)*1/s$ where s represents the LaPlace transform variable so that the function 1/s indicates an integration process. The amplitude of the transfer function G(s) as a function of the frequency f with s=2*pi*f*j is:

$|G(f)| = |1/(m*(2*pi*f*j)^2 + b*2*pi*f*j)|$ where j is the imaginary unit and |.| is the modulus operation on complex numbers.

The phase of the transfer function G(s) as a function of the frequency f with s=2*pi*f*j is:

$phase(G(f)) = phase(1/(m*(2*pi*f*j)^2 + b*2*pi*f*j))$ with the phase(.) function returning the phase of the complex number in its argument.

The parameter m representing the total joint mass or inertia used and the parameter b representing the total joint linear viscous drag force or torque in the joint dynamic model can be computed by fitting the average values as determined empirically. The preferred method in making such determination is a system parameter identification procedure based on collecting for several cycles the joint position trajectory Joint_position_traj (k*T) and the joint motor torque trajectory Joint_motor_torque_traj (k*T) while the joint is tracking under position servo control, a set of sinusoidal position commands of excitation frequencies f_exc in the range of interest for the application (typically 1 Hz to 200 Hz) with the manipulator in one or more reference configurations for the application. The parameter T is the sampling time used to collect the trajectory in a digital discrete signal format in computer equipment. For each excitation frequency, the amplitudes A_motor_torque (f_exc) and A_position(f_exc) and the phase Phi_motor_torque(f_exc) and Phi_position(f_exc) of the sinusoidal approximations:

Joint_motor_torque_traj(k*T)=A_motor_torque(f_exc)*sin(2*pi*f_exc*k*T+Phi_motor_torque(f_exc), Joint_position_traj(k*T)=A_joint_position(f_exc)*sin(2*pi*f_exc*k*T+Phi_joint_position(f_exc)

of respectively the joint motor torque trajectory and the joint position trajectory are determined with a data fit based on the minimization of the sum of the square error between the collected samples Joint_motor_torque_traj (k*T) and Joint_position_traj (k*T) with the above expression. Such a minimization can be carried out with well known Least Square Error Optimization methods. An experimental measure of the joint motor torque to joint position transfer function gain |G_exp(f_exc)| is then obtained for each excitation frequency as the ratio:

|G_exp(f_exc)|=A_position(f_exc)/A_motor_torque (f_exc), and the joint motor torque to joint position transfer function phase phase(G(f_exc)) is then obtained for each excitation frequency as the difference:

phase(G_exp(f_exc))=Phi_position(f_exc)−Phi_motor_torque(f_exc).

The total joint inertia or mass parameter m and the total joint viscous drag b are then computed to minimize the square error between the experimentally determined amplitude of the transfer function |G_exp(f_exc)| and the model transfer function |G(f_exc)| over the set of frequency f_ext used to excite the system.

The observer 207 used in the control system 200 can be realized from the state space model of the Dynamic Joint Model in the general form:

$x\_obs(t) = (A - L*Cobs)x\_obs(t) + L*y(t) + B*u(t)$ where L is the 3×1 column vector of observer gains l1, l2 and l3 whose values are set as a function of the desired speed of convergence of the observer estimations to their real values and the desired level of noise-reducing averaging on the observer estimations;

$L = [l1\ l2\ l3]$;

Cobs is the 3×1 row vector:

C_obs=[1 0 0];

x_obs(t) is the 3×1 column vector with first element being the observed joint position, second element being the observer joint velocity, and third element being the observed External Torque; and y(t) is the joint position as measured by the joint position sensor.

Figure 3:
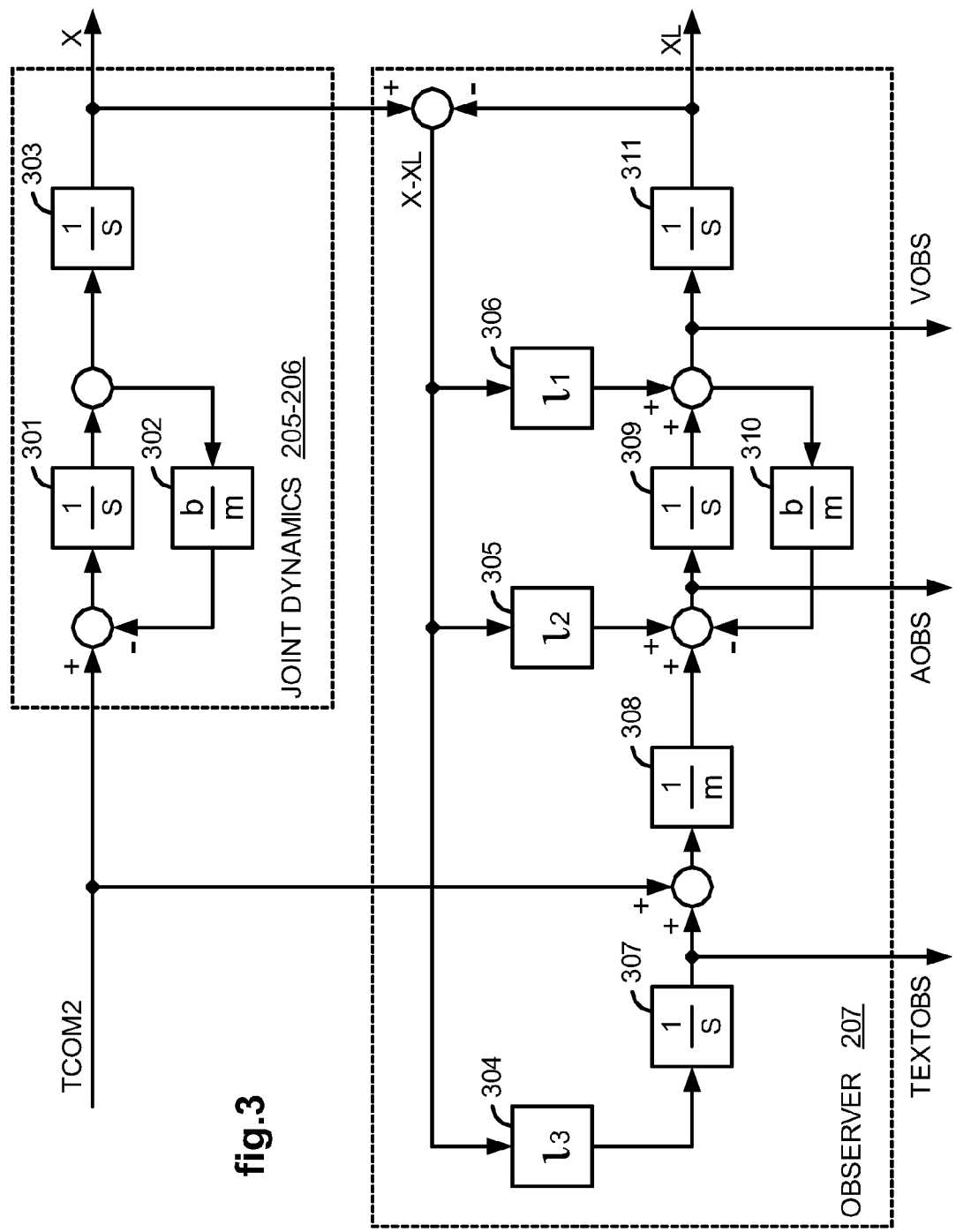
FIG. 3 illustrates a block diagram of an observer used in a control system for reducing internally generated frictional and inertial resistance to manual positioning of a slave manipulator, utilizing aspects of the present invention.

FIG. 3 illustrates, as an example, a block diagram of the observer 207 used in the control system 200 which is equivalent to the state space description of the observer given above with the only addition of an observed acceleration output computed as a finite difference of successive velocity observations. For the construction of the observer 207, the rigid joint dynamic model described above is assumed for modeling the joint dynamics, which in this case, includes the response of the joint motor 205 to the third torque command, response of the joint to the joint motor 205, and sampling of the resulting joint displacement by the joint sensor 206.

Conversion to digital form using the "Z" transform can be done employing a number of state of the art techniques (see for example "Control System Design" Graham C. Goodwin, Stefan F. Graebe, Mario E. Salgado, Prentice Hall 2001) such as the Zero Holder Hold Method, the Tustin Transform Method or the Discrete Delta Transform. The Discrete Delta Transform is the preferred method as it provides a smooth transition from continuous time to discrete time at the fast sampling rates (such as around 1 KHz in the present example) available with modern computers.

The observer 207 estimates a torque "TEXTOBS" being applied against and/or commanded to drive the joint motor 205 which is stored in the integrator state 307, estimates an acceleration "AOBS" which serves as an input to integrator 309, and a velocity "YOBS" which serves as an input to integrator 311, from a model of the joint and joint motor. The observer 207 is a tunable third order system having two complex poles setting the bandwidth of the observer 207 and a real pole setting the speed of estimation of the torque being applied against and/or commanded to drive the joint motor 205. Tuning in this example may be performed by adjusting values for gains l1 304, l2 305 and l3 306 to achieve the desired placement for the observer poles according to well known formulas for pole placement (see for example "Control System Design" Graham C. Goodwin, Stefan F. Graebe, Mario E. Salgado, Prentice Hall 2001)

A second Dynamic Joint Model that proves itself useful for the estimation of the joint velocity, joint acceleration and the external torque applied to the joint in presence of significant flexibility in the link mechanical structure and drive train is a fifth order dynamic system representing two masses or inertias interconnected by a visco-elastic spring wherein the first mass has applied to it a viscous drag force linearly proportional to its velocity and the second mass has applied to it an external constant bias torque (External Torque). The first mass represents the motor inertia and the second mass represents the link inertia. The resonance frequency of the model resulting from the interplay of the two masses and the intervening spring captures the mechanical resonance of the joint. Choosing as system states the joint position of the first mass (motor mass), the joint velocity of the first mass, the joint position of the second mass (link mass), the joint velocity of the second mass, and the External Torque; and as system input, the torque applied by the joint motor to the motor mass (Motor Torque), the second Dynamic Joint Model can be described in state space as:

$$dx(t)/dt = Ax(t) + Bu(t)$$

$$y(t) = Cx(t)$$

wherein the input u is a scalar representing the Motor torque; the output y is a 3×1 column vector with first element being the motor joint position, second element being the motor joint velocity, and third element being the External Torque; the state x is a 5×1 column vector with first element being the motor position, second element being the motor velocity, third element being the link position, fourth element being the link velocity and fifth element being the External Torque; A is a 5×5 matrix (state matrix) given by:

$$A = [0\ 1\ 0\ 0\ 0;\ 0\ 0\ b1\ b2\ 0;\ 0\ 0\ 0\ wp\ 0;\ 0\ 0\ -wp\ 2*\mathrm{delta}*wp]$$

with delta being the damping coefficient of the joint mechanical resonance, wp being the natural frequency in radians of the joint mechanical resonance, wz being the natural frequency in radians of the zeros associated to the transfer function between the motor torque and motor position, and b1 and b2 determinable using the following expressions:

$$b1 = 1 - wp^2/wz^2,$$

$$b2 = 2*\mathrm{delta}*(wp^2/wz^2 - Wp/Wz);$$

B is a 5×1 column vector equal to:

$$B = [0\ 1/m*wp^2/wz^2\ 0\ wp/m]$$

with m the total mass of the joint sum of the motor mass and the link mass; and
C is a 5×5 identity matrix equal to:

$$C = [1\ 0\ 0\ 0\ 0;\ 0\ 1\ 0\ 0\ 0;\ 0\ 0\ 1\ 0\ 0;\ 0\ 0\ 0\ 1\ 0;\ 0\ 0\ 0\ 0\ 1].$$

The transfer function G(s) between the joint position and the joint motor torque can be expressed using the second Dynamic Joint Model presented above as:

$$G(s) = 1/(m*s^2)*(Wp/Wz)^2*(s^2 + 2*\mathrm{delta}*wz*s + wz^2)/(s^2 + 2*\mathrm{delta}*wp\ s + wp^2)$$

A methodology identical to the one described above for the first Dynamic Model can be employed to obtain empirically derived values for the parameters of the second Dynamic Model and to design an observer to obtain estimates of the joint motor position, velocity, acceleration and external torque.

The non-linear viscosity model 201 is designed to mask the velocity dependent drag force or torque that can be felt in the joint of the slave manipulator 128 when the slave manipulator 128 is manually moved around to reach its desired position at the surgical site. The drag force or torque exhibits different functional dependencies on the joint velocity according to the specific mechanical design of the joint. The actual value of the joint drag force or torque can be empirically determined at a number of joint velocities of interest for the application. The measurement at each one of the desired velocities can be for example carried out by driving the joint over most of its range of motion at the desired constant velocity using a servo position control system to regulate the joint velocity to closely track the desired one. The motor torque commanded by the servo position control system along the constant velocity part of the trajectory can be collected and averaged to produce the desired measurement of the drag force or torque at the specific desired velocity.

In a first implementation of the non-linear viscosity model 201, the empirically determined values of viscous drag force or torque for each velocity of interest are compiled in a look-up table with linear or quadratic interpolation to provide an actual viscous drag force or torque output tau_viscous based on the observed velocity:

$$\mathrm{tau\_viscous} = \mathrm{lookupTable}(vobs)$$

In a second implementation of the non-linear viscosity model 201, a polynomial functional relationship between joint velocity and viscous drag torque or force is assumed:

$$\mathrm{tau\_viscous} = c1*v\_obs + c3*v\_obs^3 + c5*v\_obs^5$$

where the coefficients c1, c3 and c5 are determined to minimize the square error between the polynomial model and the experimentally determined values of viscous drag force or torque for each velocity of interest.

The actual output of the viscosity model 201 is meant to compensate for a desired percentage viscous_gain of the overall viscous drag forces or torque described above according to the relationship:

$$\mathrm{tau\_viscous\_comp} = \mathrm{viscous\_gain}*\mathrm{tau\_viscous}$$

It will be appreciated that, by aiming only at a partial compensation of the viscous forces, the feeling experienced by the Assistant when manually positioning the slave manipulator 128 becomes lighter without incurring the risk of triggering active behaviors, i.e. the feeling that the manipulator tends to move away on its own once its motion is manually initiated, that may arise when the total viscous force in the joints are compensated for. At the same time the requirements on the accuracy of the viscosity model 301, that in practice always change with operating temperature and age of the slave manipulator 128, are also greatly relaxed.

Figure 4:
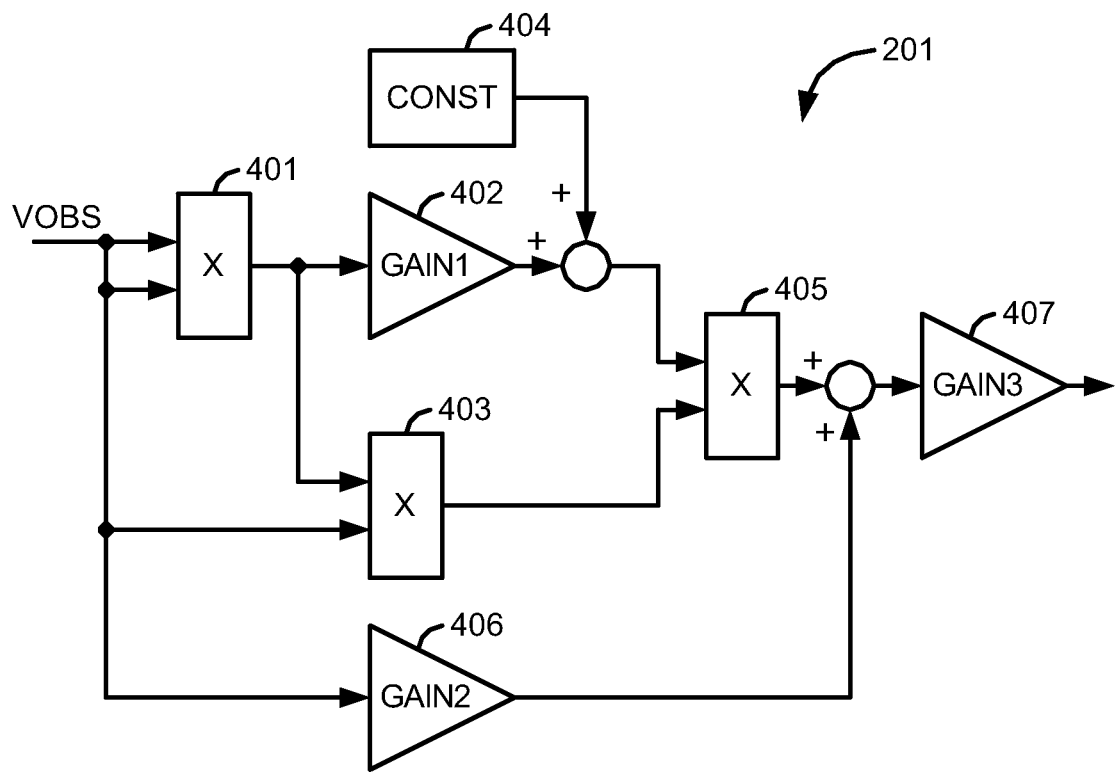
FIG. 4 illustrates a block diagram of a non-linear viscosity model used in a control system for reducing internally generated frictional and inertial resistance to manual positioning of a slave manipulator, utilizing aspects of the present invention.

FIG. 4 illustrates, as an example, a block diagram of the non-linear viscosity model 201 that makes use of the polynomial viscosity model. In this model, blocks 401, 403, 405, and 407 represent product functions. The gain GAIN1 402 is equal to c5, the GAIN2 406 is equal to c1, the constant CONST 404 is equal to c3, and the GAIN3 407 is equal to the viscous_gain of the prior described equations.

The inertial forces arising at the joints from the rigid body mechanics of the slave manipulator 128 are a non-linear function of the positions, velocities and acceleration of all the "n" manipulator joints. The analytical equation describing such inertial forces/torque tau_inertial is (see, e.g., "Introduction to Robotics" John J. Craig, 1989 Prentice Hall):

$$\text{tau\_inertial} = Ma(\text{pos})*acc + \text{Cor}(\text{pos}, \text{vel})$$

where Ma(pos) is the n×n manipulator inertial matrix; Cor (pos, vel) is the n×1 vector of centripetal and Coriolis forces; pos, vel, acc are respectively the n×1 vector of manipulator joint positions, velocities and accelerations. Both Ma(pos) and Cor(pos, vel) are a nonlinear function of the manipulator link masses, baricentral inertias and center of mass locations.

The inertial model 203 in meant to compensate for a desired percentage m gain of the overall inertial forces described above according to:

$$\text{tau\_inertial\_comp} = m\_gain * \text{tau\_inertial}$$

It will be appreciated that, by aiming only at a partial compensation of the inertial forces, the feeling experienced by the Assistant when manually positioning the slave manipulator 128 becomes lighter without incurring the risk of triggering unstable behaviors that may arise from attempts to mask the whole manipulator inertia. At the same time the requirements on the accuracy of the model and the inertial parameters in the inertial model 203 are also greatly relaxed.

The inertial model 203 can be further greatly simplified considering that the manual positioning of the surgical instrument 138 usually only requires slave manipulator movements at relatively slow speeds and accelerations during which the cross influence between joints, the centrifugal forces and the Coriolis forces are negligible.

Figure 5:
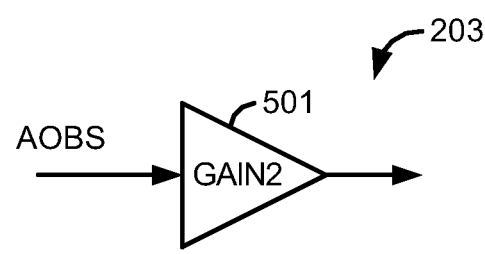
FIG. 5 illustrates a block diagram of an inertia model used in a control system for reducing internally generated frictional and inertial resistance to manual positioning of a slave manipulator, utilizing aspects of the present invention.

FIG. 5 illustrates, as an example, a block diagram of the inertia model 203. In this example, the inertia model 203 is simply reduced to a gain 501 that is the product of the joint inertia M identified above and the desired percentage m_gain of inertial compensation:

$$\text{Gain} = m\_gain * M.$$

Figure 6:
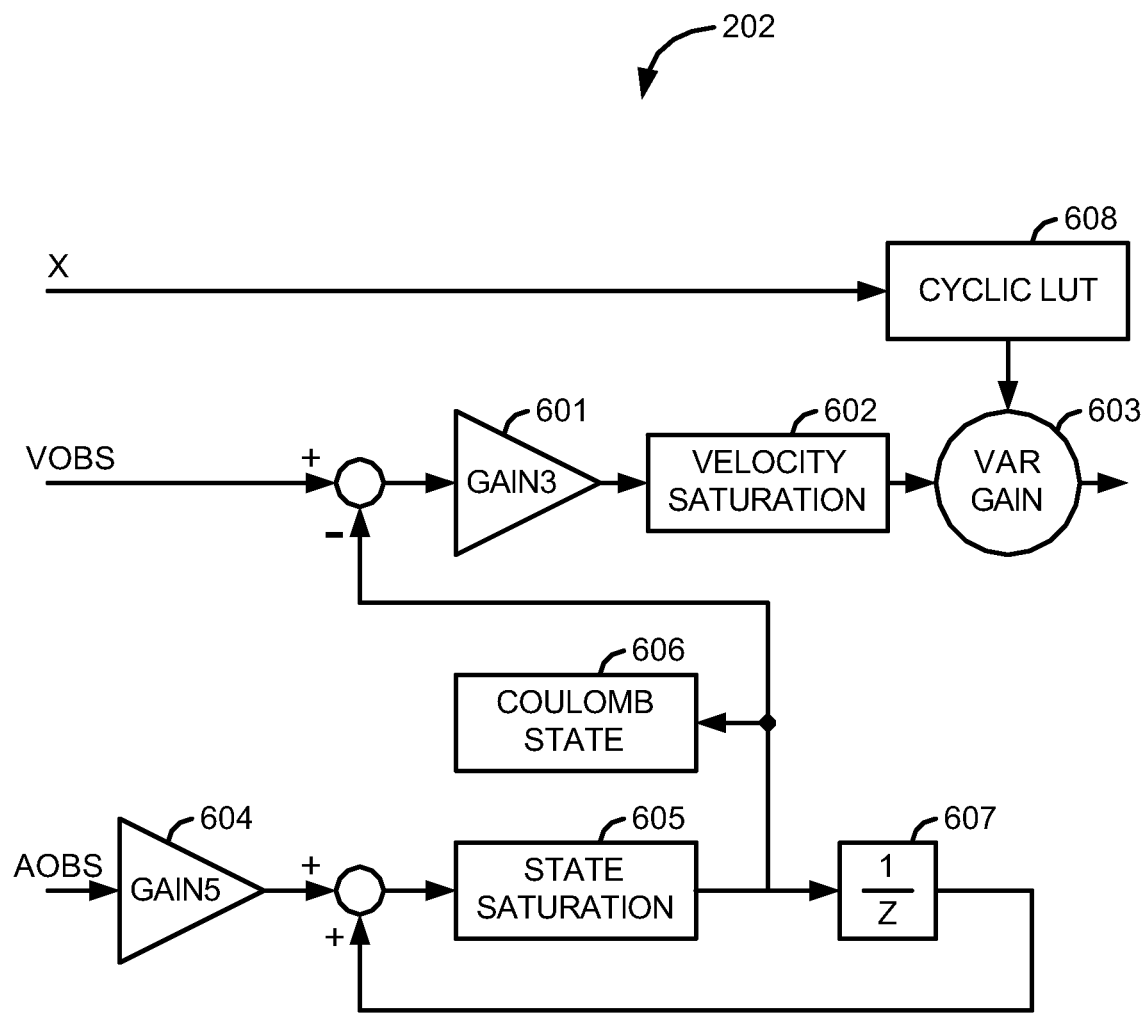
FIG. 6 illustrates a block diagram of a Coulomb with hysteresis and cogging compensation model used in a control system for reducing internally generated frictional and inertial resistance to manual positioning of a slave manipulator, utilizing aspects of the present invention.

FIG. 6 illustrates, as an example, a block diagram of the Coulomb with Hysteresis and Cogging Compensation Model 202, responding to the joint position "X" as well as the estimated velocity "YOBS" and estimated acceleration "AOBS" generated by the observer 207. The model is in digital transform form, as evidenced by the Z-transform term "1/Z" for the one cycle delay function 607. The model is composed of three logical blocks, one implementing an algebraic Coulomb Friction model (including sub-blocks 601, 602), one implementing a dynamic model with an internal state to represent the hysteretic behavior of friction at changes in the direction of the joint motion (including sub-blocks 604, 605, 606, 607), and one compensating for cyclical cogging effects (including sub-blocks 603, 608).

Figure 7:
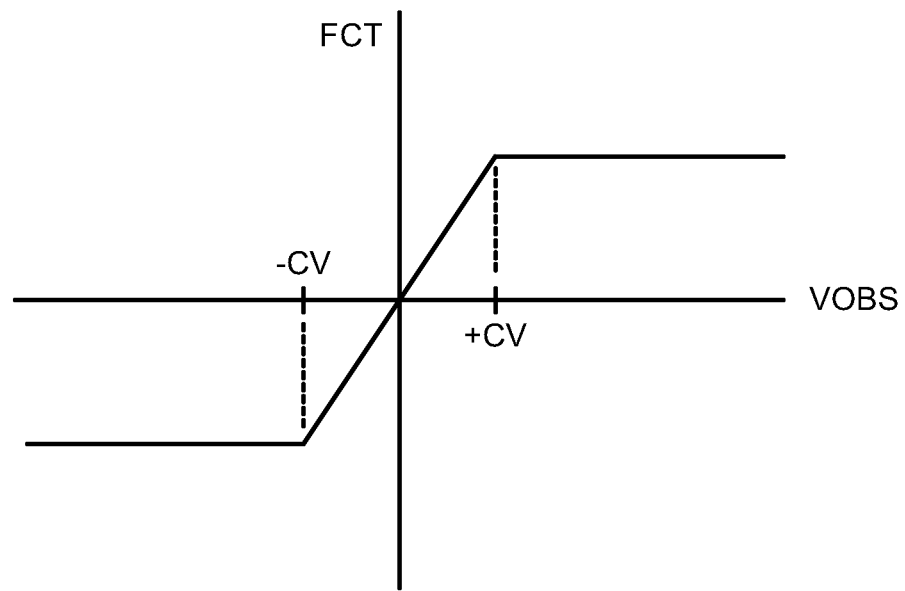
FIG. 7 illustrates a graph of the Coulomb model without hysteresis for use in a control system for reducing internally generated frictional and inertial resistance to manual positioning of a slave manipulator, utilizing aspects of the present invention.

The first logical block of the model 202 in the top part of FIG. 6 includes the gain block GAIN3 601 representing the inverse of the corner velocity which effectively scales the input velocity so that the corner velocity corresponds to unity; the unitary velocity saturation block 602 that limits its output to be 1 if it is larger than one, and −1 if less then −1 and otherwise produces in output a copy of its input; and the gain block GAIN4 603 that is the actual maximum value of the joint Coulomb Friction torque or force that the model 202 is compensating for whenever the joint velocity is above the corner velocity. The resulting output friction compensating torque "FCT" as a function of the input velocity VOBS is shown in FIG. 7. It will be appreciated that the lower the corner velocity ("CV"), the faster the full Coulomb Friction torque will be delivered to the joint to cancel quickly the joint friction when the joint motion is initiated. A limit to how low the corner velocity can be practically chosen is determined experimentally to prevent self oscillations that may arise as a result of the linear part of the model 202 behaving as a positive velocity feedback gain.

Figure 8:
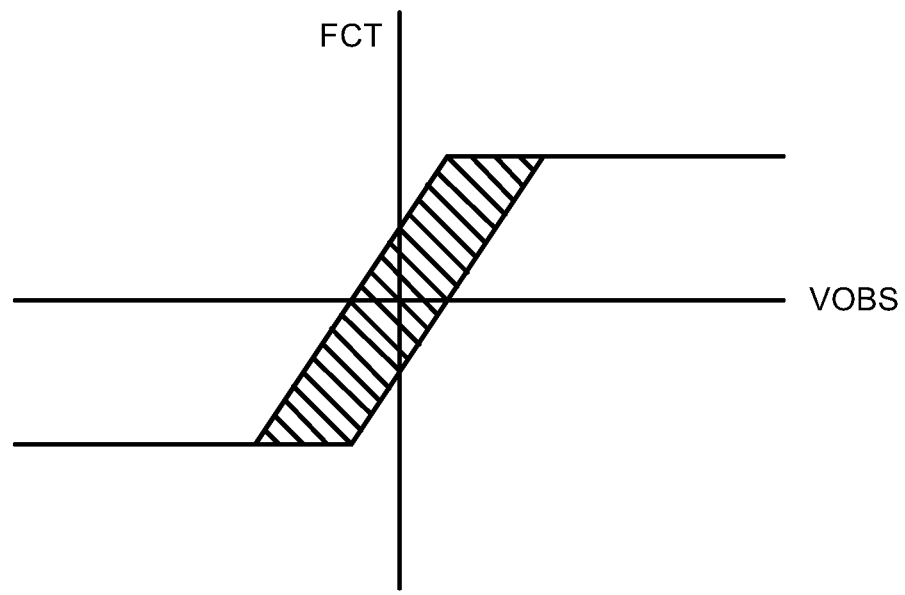
FIG. 8 illustrates a graph of the Coulomb with hysteresis model used in a control system for reducing internally generated frictional and inertial resistance to manual positioning of a slave manipulator, utilizing aspects of the present invention.

The second logical block of the model 202 in the bottom part of FIG. 6 includes: a Coulomb State Gain block 604 that multiplies the observed joint acceleration AOBS, a state saturation block 605 that limits the value that can get stored in the state memory block 606 to a Coulomb_state_max value. The effect of the second part of the model is to modify the output friction compensating torque FCT as a function of the input velocity VOBS in FIG. 7 to include an hysteresis band as in FIG. 8 that makes the output friction compensating torque change around the zero input velocity more or less rapidly for rates of change of velocity respectively higher or lower. The benefit provided by the second part of the model 202 is to allow the use of lower corner velocities, i.e. higher values for the corner velocity inverse gain 601 than it would be possible using the first part of the model alone without incurring the above mentioned self oscillations. The use of lower corner velocities in turn means that a greater percentage of the Coulomb friction is compensated at low speeds and the slave manipulator joint feels lighter to the Assistant during precise manual positioning tasks that typically are carried out at low velocities.

The third logical block of the model 202 in the top-right part of FIG. 6 includes: a variable gain 603 whose value is determined by the current joint position "X" and a lookup table ("LUT") 608. As the joint moves during manual positioning of the slave manipulator 128 by the Assistant, resistance to such movement may periodically increase as a function of the joint displacement. In case of the presence of cyclic kinematic imperfections of the drive train of the joint, the maximum value of the joint Coulomb friction can have a cyclic dependence on the joint angle. This phenomenon is commonly referred to as cogging. The cyclic lookup table 608 can be used to account for such cogging effects by providing a multiplicative gain 603 as a function of the joint position. The values for the lookup table 608 can be derived by averaging motor torque required at each joint angle to servo the joint at the slowest controllable constant velocity.

Gains GAIN3 601 for the corner velocity inverse, GAIN4 603 for the Coulomb coefficient, GAIN5 604 for the coulomb state gain, as well as values for the cyclic LUT 608 may be determined empirically as necessary, as may the corner velocity saturation 602 and state saturation 605 values.

Figure 9:
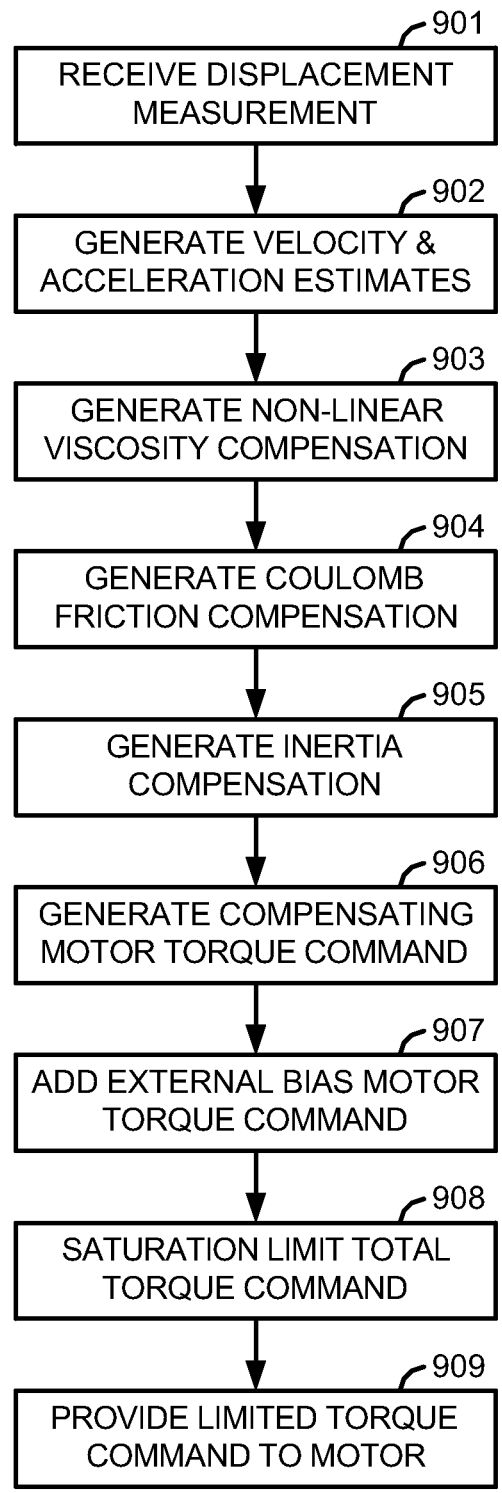
FIG. 9 illustrates a flow diagram of a method for reducing forces to be overcome when manually moving a robotic arm, utilizing aspects of the present invention.

FIG. 9 illustrates, as an example, a flow diagram of a method for reducing internally generated frictional and inertial resistance when manually positioning a slave manipulator during Clutch Mode. In this method, the slave manipulator is being manually moved in order to position and/or orient an attached surgical instrument at a surgical site within a patient while control of the slave manipulator is temporarily disengaged from the master manipulator.

In 901, a periodically sampled displacement measurement is received from a joint sensor corresponding to a selected active joint of the slave manipulator. In 902, joint angular or linear velocity and acceleration estimates are generated using the received joint displacement measurement, previously received joint displacement measurements, and a commanded joint motor torque. In 903, a non-linear viscosity compensating signal is generated using the velocity estimate. In 904, a coulomb friction with hysteresis and cogging compensating signal is generated using the joint displacement measurement, and velocity and acceleration estimates. In 905, an inertia compensating signal is generated using the angular acceleration estimate. In 906, a first friction and inertia compensating torque command is generated by adding the signals generated in 903, 904 and 905. In 907, an external bias motor torque command is added to the first friction and inertia compensating torque command, if available. In 908, the resulting signal in 907 is then saturation limited to generate a second friction and inertia compensating torque command. In 909, the second friction and inertia compensating torque command is then provided to the joint motor in order to assist in the manual movement of the slave manipulator so as to reduce internally generated frictional and inertial resistance to manual positioning of the slave manipulator to a comfortable and stability safe level. The method then continually repeats 901-909 to continually update the magnitude of the second friction and inertia compensating signal being provided to the joint motor, so that when movement of the slave manipulator ceases, the compensating signal being provided to the joint motor becomes zero.

Although the various aspects of the present invention have been described with respect to a preferred embodiment, it will be understood that the invention is entitled to full protection within the full scope of the appended claims.

What is claimed is:

1. A method for reducing internally generated frictional and inertial resistance when manually positioning a slave manipulator, the method comprising:
   controlling movement of the slave manipulator in response to input received from a master manipulator, by using a master/slave control system when the master/slave control system is engaged; and
   performing a following combination of actions when the master/slave control system is disengaged:
   receiving sampled displacement measurements corresponding to movement of a joint of the slave manipulator;
   generating a signal to compensate for at least one of: internally generated non-linear viscous friction, internally generated Coulomb friction, and internally generated inertial resistance, by using the received sampled displacement measurements; and
   driving a motor that actuates the joint by using the signal.

2. The method according to claim 1, wherein the signal is generated so as to be saturation limited.

3. The method according to claim 1, wherein the combination of actions performed when the master/slave control system is disengaged, further comprises:
   generating a velocity signal from the received sampled displacement measurements by using an observer configured as a dynamic model of the joint, and
   generating an acceleration signal from the received sampled displacement measurements by using the observer,
   wherein the signal is generated by using the velocity and acceleration signals.

4. A robotic system comprising:
   a slave manipulator having a joint and a motor which actuates the joint;
   a master manipulator;
   a master/slave control system which controls movement of the slave manipulator in response to input received from the master manipulator when the master/slave control system is engaged; and
   a processor programmed to perform the following actions when the master/slave control system is disengaged: receive sampled displacement measurements corresponding to movement of the joint of the slave manipulator; generate a signal by using the received sampled displacement measurements to compensate for at least one of internally generated non-linear viscous friction, internally generated Coulomb friction, and internally generated inertial resistance; and provide the signal to drive the motor of the slave manipulator.

5. The robotic system according to claim 4, wherein the processor is programmed to generate the signal so as to be saturation limited before providing the signal to drive the motor of the slave manipulator.

6. The robotic system according to claim 4, wherein the processor is programmed to implement an observer which is configured as a dynamic model of the joint and to perform the following additional actions when the master/slave control system is disengaged: generate a velocity signal from the received sampled displacement measurements by using the observer; generate an acceleration signal from the received sampled displacement measurements by using the observer; and generate the signal by using the velocity and acceleration signals.

* * * * *